(12) United States Patent
Cantor

(10) Patent No.: US 10,533,215 B2
(45) Date of Patent: Jan. 14, 2020

(54) NUCLEIC ACID QUANTIFICATION PRODUCTS AND PROCESSES

(75) Inventor: Charles R. Cantor, Del Mar, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 13/129,797

(22) PCT Filed: Nov. 20, 2009

(86) PCT No.: PCT/US2009/065280
§ 371 (c)(1),
(2), (4) Date: Jul. 18, 2011

(87) PCT Pub. No.: WO2010/059914
PCT Pub. Date: May 27, 2010

(65) Prior Publication Data
US 2011/0263453 A1 Oct. 27, 2011

Related U.S. Application Data

(60) Provisional application No. 61/117,474, filed on Nov. 24, 2008.

(51) Int. Cl.
*C12Q 1/68* (2018.01)
*C12Q 1/6837* (2018.01)

(52) U.S. Cl.
CPC .................. *C12Q 1/6837* (2013.01)

(58) Field of Classification Search
USPC .......... 435/6.1, 6.11, 6.12, 91.1, 91.2, 91.51, 435/287.1, 287.2; 436/94, 501; 536/23.1, 24.3, 24.33, 25.3
See application file for complete search history.

(56) References Cited

U.S. PATENT DOCUMENTS

| | | | |
|---|---|---|---|
| 5,786,146 A | 1/1998 | Herman et al. |
| 5,858,732 A | 1/1999 | Solomon et al. |
| 6,214,560 B1 | 4/2001 | Yguerabide et al. |
| 6,811,973 B1 | 11/2004 | Reich |
| 8,034,567 B2 | 10/2011 | Cantor et al. |
| 8,304,194 B2 | 11/2012 | Cantor et al. |
| 2003/0082600 A1 | 5/2003 | Olek et al. |
| 2003/0157528 A1 | 8/2003 | Remacle et al. |
| 2003/0180779 A1 | 9/2003 | Lofton-Day et al. |
| 2004/0006033 A1 | 1/2004 | Zhu |
| 2004/0081993 A1 | 4/2004 | Cantor et al. |

(Continued)

FOREIGN PATENT DOCUMENTS

| | | |
|---|---|---|
| WO | WO 03/095680 | 11/2003 |
| WO | WO 07/050990 | 5/2007 |

(Continued)

OTHER PUBLICATIONS

Anantha et al., "Porphyrin binding to quadrupled T4G4." Biochemistry. Mar. 3, 1998;37(9):2709-2714.

(Continued)

*Primary Examiner* — Frank W Lu
(74) *Attorney, Agent, or Firm* — Kilpaptrick Townsend & Stockton LLP

(57) ABSTRACT

Described herein are products and processes for nucleic acid quantification, which are in part useful for detecting and determining the nucleotide sequence of rare nucleic acids (i.e., low copy number nucleic acids) in a sample. Such products and processes are useful for reducing the dynamic range among different nucleic acid species.

16 Claims, 1 Drawing Sheet

1. Add counterpart nucleic acids to targets

| Target | Counterpart | Ratio | Total |
|---|---|---|---|
| A. 100 units | 10 units | 10 | 110 units |
| B. 10 units | 10 units | 1 | 20 units |
| C. 1 unit | 10 units | 0.1 | 11 units |

2. Compress dynamic range by array capture

3. Determine amounts of each target

(56) References Cited

U.S. PATENT DOCUMENTS

| | | |
|---|---|---|
| 2004/0203050 A1 | 10/2004 | Reich |
| 2004/0229242 A1 | 11/2004 | Carter et al. |
| 2005/0009015 A1 | 1/2005 | Ji et al. |
| 2005/0112590 A1 | 5/2005 | Boom et al. |

FOREIGN PATENT DOCUMENTS

| | | |
|---|---|---|
| WO | WO 09/091934 | 7/2009 |
| WO | WO 10/059914 | 5/2010 |

OTHER PUBLICATIONS

Beaucage and Caruthers, Tetrahedron Letts., 22:1859-1862, 1981.
Current Protocols in Molecular Biology, John Wiley & Sons, N.Y., 6.3.1-6.3.6 (1989).
Dear PH., "One by one: Single molecule tools for genomics." Brief Funct Genomic Proteomic. Jan. 2003;1(4):397-416.
Diamandis et al., Immunoassay, Chapter 9, ( Diamandis and T. K. Christopoulos eds.,) Academic Press: New York, 1996, pp. 205-225.
Gottschling et al., Bioorg. and Medicinal Chem. Lett. 11: 2997 (2001).
Gibson et al., "Nonpeptidic αvβ33 Integrin Antagonist Libraries: On-Bead Screening and Mass Spectrometric Identification without Tagging," Agnew. Chem. Int. Ed. 40(1): 165-169 Jan. 5, 2001.
Leon et al., "Evaluation of resins for on-bead screening: a study of papain and chymotrypsin specificity using PEGA-bound combinatorial peptide libraries," Bioorg. Med. Chem. Lett. 8: 2997-3002 (1998).
Margulies et al., "Genome sequencing in microfabricated high-density picolitre reactors." Nature. Sep. 15, 2005;437(7057):376-380.
Meyers & Miller, CABIOS 4: 11-17 (1989).
Needham-VanDevanter et al., "Characterization of an adduct between CC-1065 and defined oligodeoxynucleotide duplex," Nucleic Acids Res. 12:6159-6168, 1984.
Orain et al., "Solid phase synthesis of trypanothione reductase inhibitors—towards single bead screening," Tetrahedron Lett. 42: 515-518 (2001).
Papanikos et al., "alpha-Ketocarbonyl peptides: a general approach to reactive resin-bound intermediates in the synthesis of peptide isosteres for protease inhibitor screening on solid support," J. Am. Chem. Soc. 123: 2176-2181 (2001).
Pearson and Regnier, J. Chrom., 255:137-149, 1983.
Qu et al., "Analysis of drug-DNA binding data." Methods Enzymol. 2000;321:353-369.
Smith et al., "Comparison of Resin and Solution Screening Methodologies in Combinatorial Chemistry and the Identification of a 100 nM Inhibitor of Trypanothione Reductase," J. Comb. Med. 1: 326-332 (1999).
Soni et al., "Progress toward ultrafast DNA sequencing using solid-state nanopores." Clin Chem. Nov. 2007;53(11):1996-2001.
Extended European Search report and Written Opinion dated Jan. 2, 2013 in European Application No. EP09828276 filed.
International Preliminary Report on Patentability dated Jun. 3, 2011 in International Patent Application No. PCT/US2009/065280 filed, Nov. 20, 2009 and published as: WO/2010/059914 on May 27, 2010.
International Search Report and Written Opinion dated Jul. 29, 2010 in International Patent Application No. PCT/US2009/065280 filed, Nov. 20, 2009 and published as: WO/2010/059914 on May 27, 2010.

1. Add counterpart nucleic acids to targets
| Target | Counterpart | Ratio | Total |
|---|---|---|---|
| A. 100 units | 10 units | 10 | 110 units |
| B. 10 units | 10 units | 1 | 20 units |
| C. 1 unit | 10 units | 0.1 | 11 units |
2. Compress dynamic range by array capture
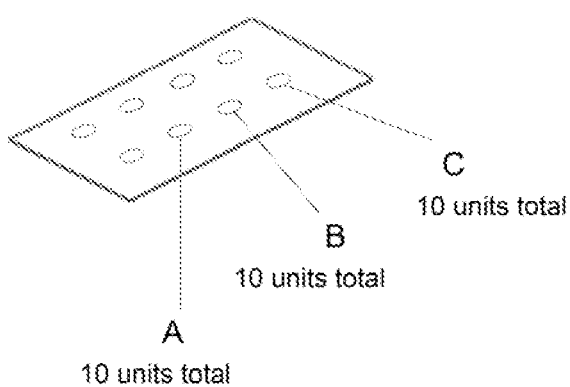
3. Determine amounts of each target

NUCLEIC ACID QUANTIFICATION PRODUCTS AND PROCESSES

RELATED PATENT APPLICATIONS

This patent application is a national stage of international patent application number PCT/US2009/065280 filed on Nov. 20, 2009, entitled NUCLEIC ACID QUANTIFICATION PRODUCTS AND PROCESSES, naming Charles R. Cantor as applicant and inventor, which claims the benefit of Provisional Patent Application No. 61/117,474 filed on Nov. 24, 2008, entitled NUCLEIC ACID QUANTIFICATION PRODUCTS AND PROCESSES, naming Charles R. Cantor as an inventor. The entire content of the foregoing patent applications is incorporated herein by reference, including all text, tables and drawings.

FIELD

The technology in part pertains to products and processes useful for quantification of nucleic acids.

BACKGROUND

Nucleic acid sequencing has become one of the main analytical techniques of modern molecular biology. The development of reliable methods for sequencing has advanced the understanding of the organization of genetic information and has made possible the manipulations of genetic material (i.e., genetic engineering). There are a variety of methods for sequencing nucleic acid molecules. Historically, the most common methods have been based on chemical (Maxam and Gilbert sequencing) or enzymatic (Sanger dideoxy sequencing and exonuclease-based sequencing) reactions that create specific truncated nucleic acid molecules that are then separated by electrophoretic techniques in order to determine their relative length. More recently, potentially higher throughput techniques, including pyro-sequencing, nanopore sequencing technology, hybridization-based sequencing methods, and the use of non-radiation based technologies for visualization of sequencing results, have been developed. It also has been proposed that scanning tunneling microscopy could be used to directly visualize the sequence of a nucleic acid molecule.

Additionally, a variety of nucleic acid detection techniques, including polymerase chain reaction (PCR), ligase chain reaction (LCR), nucleic acid sequence based amplification, strand displacement amplification, amplification with Q replicase, and numerous hybridization techniques, are utilized to detect the presence of nucleic acids of varying abundance from a variety of sources. Some strategies combine nucleic acid detection techniques with nucleic acid sequencing methods.

SUMMARY

Provided is a method for quantifying amounts of target nucleic acids of a biological sample, which comprises: (a) preparing a mixture by contacting (i) a plurality of target nucleic acids of a biological sample (targets) with (ii) a known amount of a counterpart nucleic acid for each of the targets (counterparts), where each counterpart comprises (i) a nucleotide sequence substantially identical to its target, and (ii) a feature that distinguishes each counterpart from its target, under conditions in which the targets hybridize to their counterparts; (b) compressing the dynamic range of the targets in the mixture; (c) determining the amount of each target and/or counterpart; and (d) quantifying the amount of each target by the amount in (c).

Also provided is a method for identifying target nucleic acids of a biological sample, which comprises: (a) preparing a mixture by contacting (i) a plurality of target nucleic acids of a biological sample (targets) with (ii) a known amount of a counterpart nucleic acid for each of the targets (counterparts), where each counterpart comprises (i) a nucleotide sequence substantially identical to its target, and (ii) a feature that distinguishes each counterpart from its target, under conditions in which the targets hybridize to their counterparts; (b) compressing the dynamic range of the targets in the mixture; and (c) identifying each target and/or counterpart.

Provided also is a method for compressing the dynamic range of target nucleic acids of a biological sample, which comprises: (a) preparing a mixture by contacting (i) a plurality of target nucleic acids of a biological sample (targets) with (ii) a known amount of a counterpart nucleic acid for each of the targets (counterparts), where each counterpart comprises (i) a nucleotide sequence substantially identical to its target, and (ii) a feature that distinguishes each counterpart from its target, under conditions in which the targets hybridize to their counterparts; (b) contacting the mixture with a set of capture nucleic acids, where (i) each capture nucleic acid in the set specifically hybridizes to a target and counterpart, (ii) each capture nucleic acid in the set hybridizes with substantially the same strength to the target and counterpart to which it specifically hybridizes; and (iii) the amount of each capture nucleic acid is less than highest amount of a target of the biological sample; whereby the dynamic range of the targets is compressed.

In the foregoing methods, the targets and counterparts are amplified before step (b) in certain embodiments, or the targets and counterparts are amplified after step (b) in some embodiments. In certain embodiments, the feature in the counterpart is a one-nucleotide substitution in the sequence substantially identical to its target. In some embodiments, the feature in the counterpart is one or more additional nucleotides appended to the nucleotide sequence substantially identical to its target. In certain embodiments, the ratio of the amount of each target to the amount of its counterpart is between about 1:10 and about 10:1.

In some embodiments, step (b) comprises contacting the mixture with a set of capture agents, where: each agent specifically captures each target and its counterpart, and the amount of each of the capture agents is within a range that compresses the dynamic range of the targets in the mixture. In particular embodiments, the array of capture agents is on a solid support. The capture agent interacts with the target and the counterpart with substantially equal affinity in some embodiments. In certain embodiments, each capture agent is a capture nucleic acid that comprises a polynucleotide sequence complementary to a nucleotide sequence of a target.

The target-capture agent melting temperature (Tm), in some embodiments, differs from the counterpart-capture agent Tm by less than or equal to one degree Celsius. In certain embodiments, the amounts of any two capture agents of the array differ by less than or equal to 50%.

In some embodiments, the sequence of the target is subsequently determined. The sequence of the target, in certain embodiments, is determined by a single-molecule sequencing technique (e.g., analyzing the target with a nanopore device). In some embodiments, the counterparts are separated from the targets after step (b). The counterparts or targets, in particular embodiments, comprise a capture moiety that binds to a capture agent.

Certain aspects of the technology are described further in the following drawings, detailed description and claims.

BRIEF DESCRIPTION OF THE DRAWINGS

FIG. 1 shows a non-limiting embodiment of the technology. To a composition containing nucleic acid target species is added counterpart nucleic acids, where each counterpart species hybridizes to a particular target nucleic acid species. In this particular embodiment, ten units of each counterpart species is added to targets present in a dynamic range from one unit to one hundred units. The dynamic range of targets in the sample then is compressed by capturing the target-counterpart mixture to addresses in an array that contain a capture oligonucleotide that specifically hybridizes to a target species or counterpart species. In this particular embodiment, each address of the array is capable of binding a maximum of ten units of each target or counterpart species, which decreases the dynamic range of target nucleic acids in the sample. The presence and amount of each counterpart species then is determined, and the amount of each target species can be determined in the embodiment.

DETAILED DESCRIPTION

Methods herein can be utilized to determine the abundance (e.g., relative abundance) of a nucleic acid species in a sample. Methods herein also can be utilized to determine the nucleotide sequence, and/or presence, absence or amount, of a nucleic acid species present in a sample (e.g., low copy number species). In certain nucleic acid samples, nucleic acid species can be present in a range of copy numbers where there can be a most prevalent nucleic acid species and the most rare nucleic acid species. Stated another way, certain nucleic acid species can be present in large amounts and some nucleic acid species can be present in relatively small amounts in a sample, and the nucleotide sequence, and amount, of the relatively rare nucleic acid species can be ascertained using methods provided herein. This range in the amounts of abundant species and rare species in a sample is referred to herein as the "dynamic range" of nucleic acid species amounts. In certain embodiments, methods incorporate the use of a distinct counterpart nucleic acid for each target nucleic acid of interest in a sample, and reduce the dynamic range of nucleic acid species in the sample.

Thus, methods herein confer the ability to detect low abundance, rare, or unique nucleic acid sequences in a mixed population of nucleic acid sequences, where some of the sequences are abundant. Methods herein obviate or lessen the requirement for repeatedly analyzing the same nucleotide sequences, as is sometimes the case when relatively rare nucleic acids are assessed, and thereby reduce the consumption of reagents, time and other resources.

The ability to detect and identify nucleic acids plays an important part in diagnostic analysis in many fields, including, but not limited to, medical, agriculture, military, and forensic applications. Nucleic acid detection techniques provided herein can be used as diagnostic tools, disease monitoring tools, and as prophetic tools for determining the predisposition to certain diseases or conditions, for example. It is possible to detect the presence or absence of viral or bacterial pathogens, in numerous disease conditions, using nucleic acid detection techniques herein, in some embodiments. It is also possible to detect the presence, absence or amounts of particular genes associated with certain types of cancer using nucleic acid detection techniques provided herein in certain embodiments. Methods herein also find use in monitoring bacterial contamination at food processing plants, or in soil, water and crops in agricultural settings, for example. Early detection allows for removal of contaminated foods from production lines, or might even prevent contamination if detection techniques were sensitive enough to identify potential pathogens while still low in number in the soil or water used for agriculture. Similarly, these same highly sensitive methods are of use in military or defense applications (i.e., monitoring for potential biological weapons), or forensic applications (i.e., detecting the presence of non-host nucleic acids which identify the presence of a pathogenic cause of death), for example.

Target Nucleic Acids

The term "target nucleic acids" as used herein refers to one or more nucleic acid(s) to be analyzed, detected, quantified, or sequenced (also referred to as "sample nucleic acid"). Target nucleic acids may contain one or more regions of interest. As used herein, the terms "region of interest" and "nucleotide sequence of interest" refers to nucleic acid subsequence or species addressed by processes described herein (e.g., identification, quantification, analysis). Examples of regions of interest include, without limitation, a mutation, a single nucleotide polymorphism, substitution of one or more contiguous nucleotides, deletion of one or more nucleotides, insertion of one of more nucleotides, a microsatellite, repeat nucleotide region, heterozygous allele, homozygous allele, gene sequence or subsequence, non-coding sequence or subsequence and the like.

Target nucleic acid(s) can be from any source or composition, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA and the like), and/or DNA or RNA analogs (e.g., containing base analogs, sugar analogs and/or a non-native backbone and the like). A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A target nucleic acid in some embodiments is from a single chromosome (e.g., a nucleic acid sample may be from one chromosome of a sample obtained from a diploid organism). When desired, the target nucleic acid can be altered, as known in the art, such that codons encode for a different amino acid than is normal, including unconventional or unnatural amino acids (including detectably labeled amino acids).

A target nucleic acid can comprise certain elements that can be selected according to the intended use of the nucleic acid. Any of the following elements can be included in or excluded from a target nucleic acid. A target nucleic acid, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and a selection element. A target nucleic acid may be provided with one or more of such elements. In some embodiments, a provided target nucleic acid comprises, in operable linkage, a promoter, 5'UTR, optional 3'UTR and insertion element(s) by which a target nucleotide sequence is inserted (i.e., cloned) into the template. In certain embodiments, a provided target nucleic acid comprises, in operable linkage, a promoter, insertion element(s) and optional 3'UTR, and a 5' UTR/target nucleotide sequence is inserted with an optional 3'UTR. The elements can be arranged in any order suitable for target protein production, and in some embodiments a target nucleic acid comprises the following elements, operatively linked, in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR. The terms "operatively linked" and "in operable linkage" as used herein refers to two or more nucleic acid elements (promoter, 5' UTR, 3' UTR, insertion elements, and the like) linked to each other such that each element performs its intended function, irrespective of the distance between the elements. That is, nucleic acid elements, operatively or functionally linked to each other, may be located adjacent to each other or far apart, and functionally interact.

A promoter element can be included in a target nucleic acid. A promoter often interacts with a RNA polymerase, an enzyme that catalyses synthesis of nucleic acids using a preexisting nucleic acid. When the template is a DNA template, an RNA molecule is transcribed before protein is synthesized. Certain promoters that can be utilized are of viral origin. Certain promoters are tissue specific and drive expression of the target sequence only in specific tissues. Such sequences are readily accessed by the artisan, such as by searching one or more public or private databases, for example, and the sequences are readily adapted to target nucleic acids described herein.

A 5' UTR may comprise one or more endogenous elements and may include one or more exogenous elements with respect to the target nucleic acid backbone or target sequence. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the transcription and/or translation system being utilized. A 5' UTR sometimes comprises one or more of the following elements known to the artisan: translational enhancer sequence, transcription initiation site, transcription factor binding site, translation regulation site, translation initiation site, translation factor binding site, ribosome binding site, replicon, enhancer element, internal ribosome entry site (IRES), and silencer element.

A 3' UTR may comprise one or more endogenous elements and may include one or more exogenous elements with respect to the target nucleic acid backbone or target sequence. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the transcription and/or translation system being utilized. A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

Target (or sample) nucleic acid may be derived from one or more sources. A source containing target nucleic acid(s) may contain one or a plurality of target nucleic acids. A plurality of target nucleic acids as described herein refers to at least two target nucleic acids and includes nucleic acid sequences that may be identical or different. That is, the target nucleic acids may all be representative of the same nucleic acid sequence, or may be representative of two or more different nucleic acid sequences (e.g., from 1, 2, 3, 4, 5, 6, 7, 8, 9, 10, 11, 12, 13, 14, 15, 16, 17, 18, 19, 20, 50, 100, 1000 or more sequences).

A sample may be collected from an organism, mineral or geological site (e.g., soil, rock, mineral deposit, combat theater), forensic site (e.g., crime scene, contraband or suspected contraband), or a paleontological or archeological site (e.g., fossil, or bone) for example. A sample may be a "biological sample," which refers to any material obtained from a living source or formerly-living source, for example, an animal such as a human or other mammal, a plant, a bacterium, a fungus, a protist or a virus. The biological sample can be in any form, including without limitation a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells, urine, cerebral spinal fluid and synovial fluid and organs.

Target nucleic acids may first be isolated from a sample source (e.g., cells, soil, etc) by methods known in the art. Cell lysis procedures and reagents are commonly known in the art and may generally be performed by chemical, physical, or electrolytic lysis methods. For example, chemical methods generally employ lysing agents to disrupt the cells and extract the nucleic acids from the cells, followed by treatment with chaotropic salts. Physical methods such as freeze/thaw followed by grinding, the use of cell presses and the like also may be useful. High salt lysis procedures are also commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, solution 1 can contain 15 mM Tris, pH 8.0; 10 mM EDTA and 100 ug/ml Rnase A; solution 2 can contain 0.2N NaOH and 1% SDS; and solution 3 can contain 3M KOAc, pH 5.5. These procedures can be found in Current Protocols in Molecular Biology, John Wiley & Sons, N.Y., 6.3.1-6.3.6 (1989), incorporated herein in its entirety.

A sample also may be isolated at a different time point as compared to another sample, where each of the samples are from the same or a different source. A target nucleic acid may be from a nucleic acid library, such as a cDNA or RNA library, for example. A target nucleic acid may be a result of nucleic acid purification or isolation and/or amplification of nucleic acid molecules from the sample. Target nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Target nucleic acid may comprise or consist essentially of any type of nucleic acid suitable for use with processes of the technology. Target nucleic acid often is in a form that can hybridize to a capture nucleic acid, for example. As used herein, the term "counterpart nucleic acid" refers to a nucleic acid comprising a nucleotide sequence substantially identical to the target nucleic acid, but contains a feature that distinguishes the counterpart from its target. The nucleotide sequence in the counterpart nucleic acid that is identical or substantially identical to a target nucleotide sequence, or portion thereof, allows the counterpart nucleic acid to hybridize to a capture nucleic acid with substantially the same affinity as a target nucleic acid hybridizes to the capture nucleic acid.

As used herein, the term "capture nucleic acid" refers to a nucleic acid that comprises a nucleotide sequence complimentary or substantially complementary to a nucleotide sequence in the counterpart and target nucleic acids. A capture nucleic acid can be used to capture target and counterpart nucleic acids for dynamic range compression, in certain embodiments. In some embodiments, a capture nucleic acid can be used to separate target and counterpart nucleic acid for further sequence analysis, such as nucleotide sequencing, or hybridization analysis, for example. The nucleotide sequence of the capture nucleic acid that is complimentary or substantially complementary to a nucleotide sequence in the target and counterpart nucleic acids may exist adjacent to a nucleotide sequence of interest, or may reside within or partially within the nucleotide sequence of interest. Some embodiments provide a capture nucleic acid bound to a solid support. Some embodiments provide for use of a capture nucleic acid in solution (e.g., the capture nucleic acid is not linked to a solid support), and sometimes the capture nucleic acid may be free in solution, interacted with target and counterpart nucleic acids and then linked to a solid support.

Target nucleic acid may be provided for conducting methods described herein without processing of the sample(s) containing the nucleic acid in certain embodiments. In some embodiments, target nucleic acid is provided for conducting methods described herein after processing of the sample(s) containing the nucleic acid. For example, a target nucleic acid may be extracted, isolated, purified and/or amplified from the sample(s). The term "isolated" as used herein refers to nucleic acid removed from its original environment (e.g., natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated target nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to target nucleic acid provided that contains fewer nucleic acid species than in the sample source from which the target nucleic acid is derived. A composition comprising target nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a sample to a process that linearly or exponentially generates amplicon nucleic acids having the same or substantially the same nucleotide sequence as the nucleotide sequence of the nucleic acid in the sample, or portion thereof.

Target nucleic acid also may be processed by subjecting nucleic acid to a method that generates nucleic acid fragments, in certain embodiments, before providing target nucleic acid for a process described herein. In some embodiments, target nucleic acid subjected to fragmentation or cleavage may have a nominal, average or mean length of about 5 to about 10,000 base pairs, about 100 to about 1,00 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method known in the art, and the average, mean or nominal length of nucleic acid fragments can be controlled by selecting an appropriate fragment-generating procedure by the person of ordinary skill. In certain embodiments, target nucleic acid of a relatively shorter length can be utilized to analyze sequences that contain little sequence variation and/or contain relatively large amounts of known nucleotide sequence information. In some embodiments, target nucleic acid of a relatively longer length can be utilized to analyze sequences that contain greater sequence variation and/or contain relatively small amounts of unknown nucleotide sequence information.

Target nucleic acid fragments may contain overlapping nucleotide sequences, and such overlapping sequences can facilitate construction of a nucleotide sequence of the previously non-fragmented target nucleic acid, or a portion thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample. Target nucleic acid may be partially fragmented (e.g., from an incomplete or terminated specific cleavage reaction) or fully fragmented in certain embodiments.

Target nucleic acid can be fragmented by various methods known to the person of ordinary skill, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment target nucleic acid include, without limitation, contacting target nucleic acid with apparatus that expose nucleic acid to shearing force (e.g., passing nucleic acid through a syringe needle; use of a French press); exposing target nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Target nucleic acid may be specifically cleaved by contacting the nucleic acid with one or more specific cleavage agents. The term "specific cleavage agent" as used herein refers to an agent, sometimes a chemical or an enzyme, that can cleave a nucleic acid at one or more specific sites. Specific cleavage agents often will cleave specifically according to a particular nucleotide sequence at a particular site.

Examples of enzymic specific cleavage agents include without limitation endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind II, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I.); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Target nucleic acid may be treated with a chemical agent, and the modified nucleic acid may be cleaved. In non-limiting examples, target nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, the term "complementary cleavage reactions" refers to cleavage reactions that are carried out on the same target nucleic acid using different cleavage reagents or by altering the cleavage specificity of the same cleavage reagent such that alternate cleavage patterns of the same target or reference nucleic acid or protein are generated. In certain embodiments, target nucleic acid may be treated with one or more specific cleavage agents (e.g., 1, 2, 3, 4, 5, 6, 7, 8, 9, 10 or more specific cleavage agents) in one or more reaction vessels (e.g., target nucleic acid is treated with each specific cleavage agent in a separate vessel).

Target nucleic acid also may be exposed to a process that modifies certain nucleotides in the nucleic acid before providing target nucleic acid for a method described herein. A process that selectively modifies nucleic acid based upon the methylation state of nucleotides therein can be applied to target nucleic acid. The term "methylation state" as used herein refers to whether a particular nucleotide in a polynucleotide sequence is methylated or not methylated. Methods for modifying a target nucleic acid molecule in a manner that reflects the methylation pattern of the target nucleic acid molecule are known in the art, as exemplified in U.S. Pat. No. 5,786,146 and U.S. patent publications 20030180779 and 20030082600. For example, non-methylated cytosine nucleotides in a nucleic acid can be converted to uracil by bisulfite treatment, which does not modify methylated cytosine. Non-limiting examples of agents that can modify a nucleotide sequence of a nucleic acid include methylmethane sulfonate, ethylmethane sulfonate, diethylsulfate, nitrosoguanidine (N-methyl-N'-nitro-N-nitrosoguanidine), nitrous acid, di-(2-chloroethyl)sulfide, di-(2-chloroethyl)methylamine, 2-aminopurine, t-bromouracil, hydroxylamine, sodium bisulfite, hydrazine, formic acid, sodium nitrite, and 5-methylcytosine DNA glycosylase. In addition, conditions such as high temperature, ultraviolet radiation, x-radiation, can induce changes in the sequence of a nucleic acid molecule. Target nucleic acid may be provided in any form useful for conducting a sequence analysis or manufacture process described herein, such as solid or liquid form, for example. In certain embodiments, target nucleic acid may be provided in a liquid form optionally comprising one or more other components, including without limitation one or more buffers or salts selected by the person of ordinary skill.

Counterpart Nucleic Acids

Counterpart nucleic acids are representative of each of the targets of interest in a sample population. That is, for each target nucleic acid species of interest in a sample population there is a corresponding counterpart nucleic acid, which is at least in part substantially identical and contains a feature that distinguishes the counterpart from its target. As described above for target nucleic acids, counterpart nucleic acids may by any type of nucleic acid, naturally occurring or synthetic, may be from any source or composition, and can be in any form.

The presence, absence or amount of a counterpart nucleic acid can be determined by detecting the presence, absence or amount of the one or more features that distinguish the counterpart from the target nucleic acid. In some embodiments, a feature that distinguishes a counterpart from its target is a substitution of one or more nucleotides relative to the target, which may be detected by a sequence determination method, for example. In some embodiments a feature that distinguishes a counterpart from its target is the addition or deletion of one or more nucleotides relative to the target. In some embodiments a feature that distinguishes a counterpart from its target is the substitution, deletion or addition of nucleotides in the complimentary sequence (e.g. target nucleic acid or capture nucleic acid). In some embodiments a feature that distinguishes a counterpart from its target is the presence, absence or substitution of nucleotides in sequences adjacent to a complementary sequence (e.g., directly connected or spaced by a spacer sequence in the target or capture nucleic acids).

In some embodiments, counterpart nucleic acids may also include one or more capture agents. Non-limiting examples of capture agents useful for processes described herein include without limitation any member of a binding pair, where one member of the pair is in association with a solid phase and another member of the binding pair is association with the counterpart nucleic acid. In some embodiments, a target nucleic acid may comprise a capture agent, and sometimes a counterpart nucleic acid includes one type of capture agent and a target nucleic acid includes another type of capture agent (e.g., for capturing to different solid phases). Any suitable binding pair can be utilized to effect a non-covalent interaction, including, but not limited to, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, or nucleic acid/complementary nucleic acid (e.g., DNA, RNA, PNA). Any suitable binding pair can be utilized to effect a covalent linkage, including, but not limited to, a chemical reactive group/complementary chemical reactive group (e.g., sulfhydryl/maleimide, sulfhydryl/haloacetyl derivative, amine/isotriocyanate, amine/succinimidyl ester, and amine/sulfonyl halides). Methods for attaching such binding pairs to reagents and effecting binding are known.

The term "solid support" or "solid phase" as used herein refers to a wide variety of materials including solids, semisolids, gels, films, membranes, meshes, felts, composites, particles, and the like typically used by those of skill in the art to sequester molecules. The solid phase can be non-porous or porous. Suitable solid phases include those developed and/or used as solid phases in solid phase binding assays. See, e.g., chapter 9 of Immunoassay, E. P. Diamandis and T. K. Christopoulos eds., Academic Press: New York, 1996, hereby incorporated by reference. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997 (1998); Kessler et al., Agnew. Chem. Int. Ed. 40: 165 (2001); Smith et al., J. Comb. Med. 1: 326 (1999); Orain et al., Tetrahedron Lett. 42: 515 (2001); Papanikos et al., J. Am. Chem. Soc. 123: 2176 (2001); Gottschling et al., Bioorg. And Medicinal Chem. Lett. 11: 2997 (2001). In some embodiments a solid support may be provided in a collection of solid supports. A solid support collection comprises two or more different solid support species. The term "solid support species" as used herein refers to a solid support in association with one particular solid phase nucleic acid species or a particular combination of different solid phase nucleic acid species. In certain embodiments, a solid support collection comprises 2 to 10,000 solid support species, 10 to 1,000 solid support species or about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 unique solid support species. The solid supports (e.g., beads) in the collection of solid supports may be homogeneous (e.g., all are Wang resin beads) or heterogeneous (e.g., some are Wang resin beads and some are magnetic beads).

A counterpart nucleic acid may be from a nucleic acid library, such as a cDNA or RNA library, or may contain sequences representative of those sequences found in a nucleic acid library, such as a cDNA or RNA library, for example. A target nucleic acid may be a result of nucleic acid purification or isolation and/or amplification of nucleic acid molecules from a sample. Counterpart nucleic acids provided for sequence analysis processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

In some embodiments counterpart nucleic acids are synthetic. Synthetic counterpart nucleic acids may be made by any process known in the art, which produces nucleic acids useable in the embodiments described herein. Counterpart nucleic acids may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984, for example. Purification of oligonucleotides can be effected by native acrylamide gel electrophoresis or by anion-exchange high-performance liquid chromatography (HPLC), for example, as described in Pearson and Regnier, J. Chrom., 255:137-149, 1983.

Counterpart nucleic acids, naturally occurring or synthetic, may be quantified, for example after synthesis and purification, after PCR amplification, or at any step of a process described herein, using any suitable method known in the art. For example, measuring the intensity of absorbance of a DNA solution at wavelengths 260 nm and 280 nm is used as a measure of DNA purity. DNA absorbs ultraviolet (UV) light at 260 and 280 nm, and aromatic proteins absorb UV light at 280 nm; a pure sample of DNA has the 260/280 ratio at 1.8 and is relatively free from protein contamination. A DNA preparation that is contaminated with protein will have a 260/280 ratio lower than 1.8. Quantitative PCR (Q-PCR) processes are known in the art for determining the amount of a particular DNA sequence in a sample. Also, DNA can be quantified by cutting with a restriction enzyme, electrophoresing products in an agarose gel, staining with ethidium bromide or a different stain and comparing the intensity of the DNA with a DNA marker of known concentration. Nucleic acid also can be quantified by diphenylamine (DPA) indicators by spectrometric detection at 600 nm and use of a standard curve of known nucleic acid concentrations.

Synthetic counterpart nucleic acids may be designed based upon a target species nucleotide sequence. A portion or all of a counterpart nucleic acid, naturally occurring or synthetic, may be substantially identical to its representative target nucleic acid. In some embodiments a portion or all of a counterpart nucleic acid, naturally occurring or synthetic, may contain regions that are substantially complementary to capture nucleic acids. As referred to herein, "substantially identical" with respect to sequences refers to nucleotide sequences sharing a certain amount of sequence identity to each other, counterpart nucleic acids and target nucleic acids for example. Included are counterpart, target and capture nucleotide sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

As referred to herein, "substantially complementary" with respect to sequences refers to nucleotide sequences that will hybridize with each other. The stringency of the hybridization conditions can be altered to tolerate varying amounts of sequence mismatch. Included are regions of counterpart, target and capture nucleotide sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Calculations of sequence identity can be performed as follows. Sequences are aligned for optimal comparison purposes (e.g., gaps can be introduced in one or both of a first and a second nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides at corresponding positions, respectively, are then compared among the two sequences. When a position in the first sequence is occupied by the same nucleotide as the corresponding position in the second sequence, the nucleotides are deemed to be identical at that position. The percent identity between the two sequences is a function of the number of identical positions shared by the sequences, taking into account the number of gaps, and the length of each gap, introduced for optimal alignment of the two sequences. Comparison of sequences and determination of percent identity between two sequences can be accomplished using a mathematical algorithm. Percent identity between two nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Percent identity between two nucleotide sequences can be determined using the GAP program in the GCG software package (available at the World Wide Web URL gcg.com), using a NWSgap-dna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Another manner for determining whether two nucleic acids are substantially identical is to assess whether a polynucleotide homologous to one nucleic acid will hybridize to the other nucleic acid under stringent conditions. Hybridization, under stringent conditions, also may be used to determine whether two nucleic acids are substantially identical to each other. As used herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Sometimes, stringent hybridization conditions are hybridization in 6× sodium chloride/sodium citrate (SSC) at about 45° C., followed by one or more washes in 0.2×SSC, 0.1% SDS at 65° C. Often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile.

Counterpart nucleic acids also may be modified or made as derivatives, variants and analogs of RNA or DNA made from nucleotide analogs, single (sense or antisense) and double-stranded polynucleotides, in some embodiments. It is understood that the term "nucleic acid" does not refer to or infer a specific length of the polynucleotide chain, thus nucleotides, polynucleotides, and oligonucleotides are also included. Counterpart nucleic acids may comprise or consist essentially of any type of nucleic acid suitable for use with processes of the technology, such as counterpart nucleic acid that can hybridize to a target nucleic acid, or a capture nucleic acid, for example.

Counterpart nucleic acids can include a detectable label in some embodiments. In some embodiments, a target nucleic acid can include a detectable label, and sometimes a target nucleic acid includes one type of detectable label and a counterpart nucleic acid includes a distinguishably different detectable label. When desired, the nucleic acid can be modified to include a detectable label using any method known to one of skill in the art. The label may be incorporated as part of the synthesis, or added on prior to using the counterpart nucleic acid in any of the processes described herein. Incorporation of label may be performed either in liquid phase or on solid phase. In some embodiments the detectable label may be useful for detection of targets. In some embodiments the detectable label may be useful for the quantification of bound or unbound nucleic acids (e.g., hybridized or un-hybridized counterpart). In some embodiments more than one detectable label may be used to label counterparts or targets. The use of more than one detectable label (e.g., different types of labels) may facilitate the detection or quantification of target and counterpart nucleic acids, bound or in solution. Any detectable label suitable for detection of an interaction or biological activity in a system can be appropriately selected and utilized by the artisan. Examples of detectable labels are fluorescent labels such as fluorescein, rhodamine, and others (e.g., Anantha, et al., Biochemistry (1998) 37:2709 2714; and Qu & Chaires, Methods Enzymol. (2000) 321:353 369); radioactive isotopes (e.g., 125I, 131I, 35S, 31P, 32P, 33P, 14C, 3H, 7Be, 28Mg, 57Co, 65Zn, 67Cu, 68Ge, 82Sr, 83Rb, 95Tc, 96Tc, 103Pd, 109Cd, and 127Xe); light scattering labels (e.g., U.S. Pat. No. 6,214,560, and commercially available from Genicon Sciences Corporation, CA); chemiluminescent labels and enzyme substrates (e.g., dioxetanes and acridinium esters), enzymic or protein labels (e.g., green fluorescence protein (GFP) or color variant thereof, luciferase, peroxidase); other chromogenic labels or dyes (e.g., cyanine), and other cofactors or biomolecules such as digoxigenin, streptavidin, biotin and the like.

Counterpart nucleic acid also may be exposed to a process that modifies certain nucleotides in the nucleic acid before providing counterpart nucleic acid for a method described herein. A process that selectively modifies nucleic acid based upon the methylation state of nucleotides therein can be applied to counterpart nucleic acid in certain embodiments.

With reference to FIG. 1, a generalized description of the methods is presented here, and will be described in more detail below. Counterpart nucleic acid (also referred to as counterpart or counterparts) is contacted with sample nucleic acid containing target nucleic acids (also referred to as target or targets) of interest, as illustrated in FIG. 1, step 1. The combination of counterpart and sample is contacted with capture nucleic acid, as shown in FIG. 1, step 2. The capture nucleic acid may be bound to a solid support, as illustrated in FIG. 1, step 2 or also may be suspended in solution. The counterparts and targets are allowed to interact with the capture nucleic acid, and subsequently an analysis is conducted, for example the amounts of each target may be determined, as illustrated in FIG. 1, step 3. Optionally, the targets also may be further analyzed by sequencing or hybridization studies.

Counterparts and targets (sample) may be contacted using any suitable method known to in the art. For example, for small sample sets, the artisan may combine the targets and counterparts manually using a single or a multichannel pipettor. For larger sets of samples or for high throughput applications using DNA chips or arrays, the methods described herein are compatible with robotic devices commonly used to automate high throughput DNA analysis. A non-limiting example of an automated or robotic device used for high throughput analysis, and compatible with the embodiments described herein, is a device referred to as the Oasis LM (produced by Telechem International, Inc. Sunnyvale Calif. 94089). This computer-driven biological workstation can be configured with up to four separate pipette tip heads with the ability to pipette 1, 8, 96, 384 or 1536 samples.

A known or predetermined amount of a counterpart nucleic acid often is introduced to a system for conducting methods described herein. In some embodiments the amount, in terms of units (e.g., amount (e.g., weight/weight, weight/volume, grams); concentration) of each counterpart added to a reaction may be kept constant, as illustrated in FIG. 1. The number of units of each counterpart often is kept constant in a reaction to enable a determination of the relative abundance of a target of interest, as well as enabling compression of the dynamic range of the nucleic acid species from a sample (discussed further below). In some embodiments the amount of each counterpart added may be varied (i.e., the number of units is not kept constant for each target in a reaction). The artisan may gain additional information by performing an analysis using differing amounts of counterpart nucleic acid. The amount of counterpart added for illustrative purposes in FIG. 1 is 10 units for each target. The sample illustrated in FIG. 1 has 3 nucleic acid species with regions of interest, targets A, B, and C. The abundance of the 3 targets ranges between about 1 unit and about 100 units, for illustrative purposes. In practice, samples may contain many more nucleic acids of interest, and abundances may vary significantly. The range in abundance for targets in a sample may be between about 1 unit and about 10 units, about 1 unit and about 50 units, about 1 unit and about 100 units, about 1 unit and about 500 units, about 1 unit and about 1,000 units, 1 unit and about 5,000 units, about 1 unit and about 10,000 units, about 1 unit and about 50,000 units, about 1 unit and about 100,000 units, about 1 unit and about 500,000 units, and between about 1 unit and 1,000,000 units. A unit as used herein with reference to a target is a functional designation and can be set at any actual physical amount by the artisan. A unit can be designated as a copy of a sequence, or 10 copies of a sequence. A unit can be defined as an amount that contains as little as 1 femtogram (fg) of nucleic acid or as much as 1 milligram (mg) of nucleic acid, and any amount in between, for example. More specifically, a unit may contain about 1 fg, about 2 fg, about 5 fg, about 10 fg, about 100 fg, about 500 fg, about 1 nanogram (ng), about 2 ng, about 5 ng, about 10 ng, about 100 ng, about 500 ng, about 1 microgram (μg), about 2 μg, about 5 μg, about 10 μg, about 100 μg, about 500 μg, or about 1 mg, and the like. The type of units can be held constant between nucleic acid species or each nucleic acid species may have its own type of unit.

Non-limiting examples of ratios of target to counterpart and the total number of units of nucleic acid added to each reaction are also illustrated in the table in FIG. 1. As illustrated in the table in FIG. 1 the ratio of target units to counterpart units is in the range of about between 10 to 1 (10:1) and 1 to 10 (1:10), for example. Any convenient ratio of target to counterpart may be used, in the range of between about 1:10 and about 10:1 in certain embodiments. That is, ratios of target to counterpart of about 1:10, about 1:9, about 1:8, about 1:7, about 1:6, about 1:5, about 1:4, about 1:3, about 1:2, about 1:1, about 2:9, about 2:7, about 2:5, about 2:3, about 2:1, about 3:10, about 3:8, about 3:7, about 3:5, about 3:4, about 3:2, about 3:1, about 4:9, about 4:7, about 4:5, about 4:3, about 4:1, about 5:9, about 5:8, about 5:7, about 5:6, about 5:4, about 5:3, about 5:2, about 5:1, about 6:7, about 6:5, about 6:1, about 7:10, about 7:9, about 7:8, about 7:6, about 7:5, about 7:4, about 7:3, about 7:2, about 7:1, about 8:9, about 8:7, about 8:5, about 8:3, about 8:1, about 9:10, about 9:8, about 9:7, about 9:5, about 9:4, about 9:2, about 9:1, about 10:9, about 10:7, about 10:3, and about 10:1, may be used to carry out methods described herein. Target to counterpart ratios outside the ranges given above may also prove useful for quantifying the relative abundance of a target species or for compressing the dynamic range of nucleic acids that are either extremely rare or extremely abundant in a mixed population.

As described above, and illustrated in FIG. 1, in some embodiments the same amount of each counterpart species can be added. In some embodiments the amounts of the target species may be determined (e.g., approximate amount), and an amount of counterpart corresponding to the amount of target can be added. That is, an amount of counterpart tailored to the calculated (or approximately determined) amount of target can be added at step 1 as illustrated in FIG. 1, and the amounts of counterpart species may differ from one another. In some embodiments, the amount of each capture nucleic acid is less than the highest amount of a target of the biological sample.

In some embodiments targets may be amplified, by PCR for example, prior to contact with counterparts. In some embodiments both targets and counterparts may be amplified subsequent to being contacted with each other. In some embodiments targets and counterparts may be amplified after dynamic range compression. That is, targets and counterparts may be amplified after the targets and counterparts have been contacted with the capture nucleic acids, present on an array for example, where the capture nucleic acids are present in amounts that allow dynamic range compression.

Dynamic Range Compression

In a mixed nucleic acid sample isolated from a sample source, certain nucleic acid species can be present in large amounts and some nucleic acid species can be present in relatively small amounts, and the nucleotide sequence, and presence, of the relatively rare nucleic acid species can be difficult to ascertain. This range in the amounts of abundant species and rare species in a sample is referred to herein as the "dynamic range" of nucleic acid species amounts. Dynamic range compression as referred to herein is a reduction in the number of copies of the nucleic acid species with the highest abundance. In certain embodiments, the number of copies of the highest abundance nucleic acid species are reduced as compared to the number of copies of the nucleic acid species with a lower or the lowest abundance, while maintaining a representative sample of each nucleic acid species of interest in the population in some embodiments. Stated another way, dynamic range compression in the latter embodiments lowers the ratio of high abundance nucleic acid species to low abundance species (high abundance:low abundance) in some embodiments. In certain embodiments, the ratio of the highest number species to the lowest number species is maintained after dynamic range compression, but the relative amounts of each species is reduced. Conditions often are selected to maintain at least one copy of each nucleic acid species of interest. Dynamic range compression also may be used to reduce the ratio of moderately abundant nucleic acid species as compared to sequences of low abundance, in certain embodiments. The act of dynamic range compression often results in reduction in the total nucleic acid in the sample used for subsequent analysis. Approaches that take advantage of dynamic range compression allow for a reduction in time and costs associated with nucleic acid analysis and sequencing, as fewer resources are allocated to analyzing and sequencing nucleic acid species that were once abundantly represented.

The amount of compression achieved by use of embodiments described herein can be tailored to the application at hand. In some embodiments, where the nucleic acid population is known with a degree of certainty, compression of all sequences to about the level of the rarest sequence allows for rapid analysis of the sequences with reduced or no repeated analysis. In some embodiments where the nucleic acid population is unknown, the ratio of highest abundance nucleic acid species may be reduced to a lesser degree, optionally allowing for a determination of whether some of a target nucleic acid is present in a sample (e.g., forensic applications). The degree of dynamic range compression can therefore be tailored to any range the artisan may require for optimal balance between time and reagent costs, and task needs.

The degree of dynamic range compression can be expressed in terms of a fold reduction of a dynamic range ratio, in some embodiments. A dynamic range ratio ($R_{dr}$) may be calculated with (i) number of copies or units of the highest abundance sequence (H), divided by (ii) the number of copies of the lower, or lowest, copy number nucleic acid in a composition (L):

$$R_{dr}=H/L.$$

The degree of dynamic range compression can be expressed by multiplying ratio $R_{dr}$ by a multiplier between about $1\times10^{-9}$ and 0.999. Therefore, the artisan may capture nearly all (e.g., values as high as about 0.999) or significantly less (e.g., values of about $1\times10^{-6}$) of a particular target/counterpart mixture. Examples of multipliers include, but are not limited to, multipliers of about $1\times10^{-7}$, about $1\times10^{-6}$, about $5\times10^{-6}$, about $1\times10^{-6}$, about $5\times10^{-4}$, about $1\times10^{-4}$, about $5\times10^{-3}$, about $1\times10^{-3}$, about $5\times10^{-2}$, about $1\times10^{-2}$, about $5\times10^{-1}$, and about $1\times10^{-1}$.

In some embodiments, the compression factor described above is not equivalent to normalization, as each individual target is not compressed relative to a particular species. In certain embodiments the compression can be equivalent to normalization, where all the species are compressed relative to a species.

In some embodiments, compression of the dynamic range may be accomplished using capture nucleic acids linked to a solid phase, including, without limitation, a nucleic acid array or DNA chip. In some embodiments, compression of the dynamic range of nucleic acids may be performed in solution. Dynamic range compression occurs when the target-counterpart mixture, as illustrated in FIG. 1, step 1, is contacted with capture nucleotides or nucleic acids, as illustrated in FIG. 1, step 2, for example. Capture nucleic acids may interact with a solid support. In some embodiments capture nucleic acids may interact with a solid support in a reversible manner, allowing the separation of target and counterpart for separate analysis, after capture for example.

In some embodiments the capture nucleic acid is present in limiting amounts, in solution or associated with an array, for example. In some embodiments capture nucleic acid is present in saturating amounts, when in solution or associated with an array, for example. In embodiments where dynamic range compression is effected by an array, capture may be to specific addresses on the array that contain a capture oligonucleotide species that specifically hybridizes to a target species and counterpart species.

Capture nucleic acid may be present (e.g., in solution or on a solid phase) in saturating amounts, or in non-saturating amounts, relative to the amount of target nucleic acid and counterpart nucleic acid. The degree of saturation can be expressed in terms of a ratio ($R_s$), in certain embodiments, where the amount of capture nucleic acid units (Cap) is divided by the amount of target nucleic acid units and counterpart nucleic acid units (T+Cpt):

$$R_s=Cap/T+Cpt.$$

In some embodiments, counterpart nucleic acid is saturating when $R_s$ is greater than 1, and often when $R_s$ is greater than 10. Thus, in some embodiments, $R_s$ can be between 1.001 and about 10 (e.g., partially saturating conditions; $R_s$ is about 2, 3, 4, 5, 6, 7, 8 or 9) and can be between about 10 and about 1,000,000 (e.g., $R_s$ is about 100, 200, 300, 400, 500, 600, 700, 800, 900, 1000, 2000, 3000, 4000, 5000, 6000, 7000, 8000, 9000, 10000, 50000, 100000, 500000). In some embodiments, counterpart nucleic acid is non-saturating when $R_s$ is less than 1, and often when $R_s$ is 0.1 or less. Thus, in some embodiments, $R_s$ can be between 0.999 and $10^{-6}$ (e.g., $R_s$ is about 0.1, 0.05, 0.001, $5\times10^{-4}$, $1\times10^{-4}$, $5\times10^{-5}$, $1\times10^{-5}$ and $5\times10^{-6}$). A saturating amount of capture agent sometimes includes amounts of capture agent that allow capture of 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more of the target and/or counterpart available for capture. In some embodiments, a non-saturating amount of capture agent may be associated with an array. A non-saturating amount of capture agent often gives rise to a compression of the dynamic range, due to capture of only a portion of the targets or complexes by the capture agents.

Dynamic range compression often is based on the effective amount of capture nucleic acid. The term "effective amount" as used herein refers to the effective amount of capture nucleic acid to which the target and counterpart nucleic acids are exposed. The effective amount of capture nucleic acid often is less than the total amount of a target nucleic acid species and its counterpart species, where the target nucleic acid species is the highest abundance species in the sample. The effective amount of a capture nucleic acid can be modulated according to the amount of time the target and counterpart nucleic acids are exposed to the capture nucleic acids under hybridization conditions. The effective amount of capture nucleic acid can be about the entire amount of the nucleic acid at a particular address on an array, for example, when the time for hybridization is relatively long (e.g., 24 to 48 hours), in some embodiments. The effective amount of capture nucleic acid can be less than the entire amount of the nucleic acid at a particular address on an array, for example, when the time for hybridization is relatively short (e.g., 1 minute), in some embodiments. Thus, the dynamic range can be compressed when capture nucleic acid is present in saturating or non-saturating amounts by selecting the amount of time, and conditions, under which the capture nucleic acids hybridize to the target and counterpart nucleic acids.

Thus, the hybridization timeframe may be manipulated to optimize dynamic range compression. In some embodiments, relatively short hybridization times may be used (e.g., about 0.5, 1, 2, 3, 4, 5, 10, 15, 20, 30, 40, 50, 60 minutes), sometimes where capture nucleic acid is saturating. In some embodiments hybridization can occur over a longer period of time (e.g. about 1, 2, 3, 4, 5, 10, 15, 20, 30, 40, 50, 60, 70, 80, 90, 100 hours, or more), sometimes when capture nucleic acid is non-saturating. Hybridization may occur at a substantially linear rate when the concentrations of the species to be hybridized are high and do not cause a rate-limiting bottleneck. Over time, as the concentration of one or both of the hybridization partners decreases below a threshold level, hybridization rate slows down and approximates an on/off equilibrium reaction. Taking advantage of hybridization rates, it is possible to adjust length of time of hybridization to selectively eliminate highly abundant species, and a time course can be readily performed to optimize hybridization times.

Capture nucleic acids are configured to interact with both target and counterpart, and in some embodiments the sequences of the counterpart and target species that hybridize to the capture nucleic acid are identical. The use of identical sequences gives rise to substantially equal interaction affinity with the capture oligonucleotide. The term "substantially equal affinity" as used herein with respect to binding of distinct nucleotide species to a common capture nucleic acid refers to binding reactions and conditions in which each target and counterpart interacts with a capture nucleic acid, with substantially the same frequency. In a particular embodiment illustrated in FIG. 1, step 2, each address of the array is capable of binding a maximum of ten units of each target-counterpart species, which decreases the dynamic range of target nucleic acids in the sample. The presence and amount of each counterpart species then is determined, and the amount of each target species can be determined.

Specific hybridization of capture oligonucleotides to a specific target species can be optimized, by hybridization conditions for example, according to the percent identity (% identity) of the capture and target nucleotide sequences, that hybridize to one another. As referred to herein, percent (%) identity is a measure of the number of identical bases in two or more nucleotide sequences when the sequences are optimally aligned and compared. Methods of determining sequence identity are described. Specific hybridization of sequences due to sufficient percent (%) sequence identity of capture and target nucleic acids sometimes include nucleotide sequences which have 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more sequence identity, so long as each capture nucleic acid in the set hybridizes with substantially the same strength, affinity, or hybridization efficiency, to the target and counterpart to which it specifically hybridizes. The strength of hybridization is due to sequences available for hybridization as well as conditions in which hybridization is performed. Optimal hybridization conditions can be dependent on length and sequence of the nucleic acids of interest, and can be readily selected (e.g., certain hybridization conditions are described herein).

In some embodiments dynamic range compression may be performed, at least partially or completely, in solution. After target and counterpart nucleic acids are contacted, a limiting effective amount of capture nucleic acid linked to a binding partner may be added to the mixture, in some embodiments. After hybridization, capture nucleic acid hybridized to target and counterpart nucleic acids can be contacted with a solid phase to which the other member of the binding partner is linked.

In some embodiments, a target nucleic acid includes a region of interest (discussed above). The nucleotide sequence of capture nucleic acids that hybridize to the target nucleic acid can be adjacent to a terminus of the region of interest, in some embodiments, and can comprise the region or interest, or a portion thereof, in certain embodiments. The term "adjacent" as used herein refers to a distance between the termini of two subsequences of 0 nucleotides. The term "adjacent" and "substantially adjacent" as used herein can refer to a distance of 1, 2, 3, 4, 5, 6, 7, 8, 9, 10 nucleotides between the termini of two subsequences.

After interaction of capture nucleic acid with a target-counterpart mixture, the nucleic acids may be treated with an agent that removes non-hybridized nucleic acid, in some embodiments. In certain embodiments, an exonuclease is utilized, which can digest molecules of nucleic acid not hybridized to the capture nucleic acids. In certain embodiments the target-capture or counterpart-capture nucleic acid complexes may be isolated, by solid phase capture, for example, if such complexes have not already been captured (e.g., by direct interaction with a solid phase array).

Hybridization conditions, including without limitation the melting temperature (Tm) of the target-capture complex and counterpart-capture complex, are considerations for optimizing dynamic range compression. Additionally, design of capture agents with the ability to distinguish between closely related species, by manipulating hybridization conditions and temperatures, gives the artisan significant power and flexibility for dynamic range compression, and sequence capture, identification and analysis. In some embodiments, the target-capture agent Tm differs from the counterpart-capture agent Tm by less than or equal to one degree Celsius. Melting point temperature differences between target-capture agent and counterpart-capture agent complexes useful for distinguishing between target and counterpart species sometimes include differences of 1 degree Celsius or less, 0.9 degree Celsius or less, 0.8 degree Celsius or less, 0.7 degree Celsius or less, 0.6 degree Celsius or less, 0.5 degree Celsius or less, 0.4 degree Celsius or less, 0.3 degree Celsius or less, 0.2 degree Celsius or less, or 0.1 degree Celsius or less. This difference in hybridization efficiency allows selective binding and subsequent capture or dynamic range compression of particular nucleic acid species based on the Tm of the target-capture agent and counterpart-capture agent complexes.

With reference to FIG. 1, for embodiments involving capture of target and counterpart to an array, the capture agents may interact with a solid phase at discrete locations, as opposed to interacting with capture agents across the entire surface of the solid support. An array prepared with capture agents associated with specific discrete locations, of an array, is illustrated in FIG. 1, step 2. Capture agents interacting with specific, discrete, locations can be referred to as having specific addresses, and the address of each location maybe defined by a row and column location. Preparing solid phase in this manner allows the artisan to perform a number of different range compressions or target and/or counterpart captures on the same array, while still allowing identification of each individual address so that parameters associated with a particular address can be preserved and determined.

In certain embodiments, the amounts of any two capture nucleic acids in a system, with substantially the same affinity for both target and counterpart nucleic acid, may differ. In certain embodiments, the amounts of capture nucleic acid in an array differ by 50% or less, 49% or less, 48% or less, 47% or less, 46% or less, 45% or less, 44% or less, 43% or less, 42% or less, 41% or less, 40% or less, 39% or less, 38% or less, 37% or less, 36% or less, 35% or less, 34% or less, 33% or less, 32% or less, 31% or less, 30% or less, 29% or less, 28% or less, 27% or less, 26% or less, 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, 10% or less, 9% or less, 8% or less, 7% or less, 6% or less, 5% or less, 4% or less, 3% or less, 2% or less, or 1% or less.

Subsequent to target and counterpart capture, counterpart nucleic acid may be separated from target at each address in certain embodiments, and only the target or the counterpart is further processed, for detection and/or sequencing for example. In some embodiments the target or counterpart can be captured by a capture agent partner linked to solid phase via a capture agent on target or counterpart. Advantages of this approach are fewer sequencing or detection events are needed to identify and analyze low abundance nucleic acid targets, which saves time and resources due to fewer sequencing reactions being wasted on highly abundant sequences.

The length of nucleic acid sequences may affect formation of target/capture complex and counterpart/capture complex. Nucleic acids isolated from samples and containing regions of interest may contain sequences of varying lengths, dependent on natural sequence length and nucleic acid breakage/cleavage during isolation and preparation. Often, increasing the length of complementary nucleotide sequences increases specificity of hybridization. In some embodiments, each target sequence of interest may also have sub-regions that are unique or better suited for hybridization. The length of target nucleic acid can be selected based on sequence composition and conditions. Target nucleic acid length can be about 5 base pairs (bp), 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1000 bp, 2000 bp, 3000 bp, 4000 bp, 5000 bp, 6000 bp, 7000 bp, 8000 bp, 9000 bp, or 10,000 by in length, in certain embodiments.

Similarly, the length of counterpart nucleic acid can be selected based on sequence composition and conditions. Counterpart nucleic acid lengths can be about 5 base pairs (bp), 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1000 bp, 2000 bp, 3000 bp, 4000 bp, 5000 bp, 6000 bp, 7000 bp, 8000 bp, 9000 bp, or 10,000 by in length, in certain embodiments.

Capture nucleic acids are of a sufficient length to include a nucleotide sequence complementary to target nucleic acid and counterpart nucleic acid and allow solid phase capture of capture/target and capture/counterpart complexes, in certain embodiments. Capture nucleic acid lengths can be about 5 base pairs (bp), 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1000 bp, 2000 bp, 3000 bp, 4000 bp, 5000 bp, 6000 bp, 7000 bp, 8000 bp, 9000 bp, or 10,000 by in length, in certain embodiments. Capture/target and capture/counterpart complexes may include no overlapping region, and in some embodiments, may include one or two overlapping regions. Overlapping regions can be about 5 base pairs (bp), 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1000 bp, 2000 bp, 3000 bp, 4000 bp, 5000 bp, 6000 bp, 7000 bp, 8000 bp, 9000 bp, or 10,000 by in length, in certain embodiments. Regions of overlap may be significantly overlapping (e.g. greater than 95 or even 99% overlap) to partially overlapping (overlap of between about 10% and 90%), to minimally overlapping.

Detection and Quantification of Target Nucleic Acid Species

After target and counterpart have been captured, target nucleic acid and counterpart nucleic acid may be subjected to further analysis, including without limitation, detection, sequencing, hybridization and quantification. In some embodiments target nucleic acid and/or counterpart nucleic acid species can be detected using a label incorporated directly onto or into the target or combined with the target by way of a hybridized capture agent.

In some embodiments target nucleic acid may be separated from counterpart nucleic acid prior to further analysis. The amount of counterpart nucleic acid can be determined with fewer reagents, and at a lower cost, where there is a relatively large amount of target nucleic acid and a relatively small amount of counterpart nucleic acid hybridized to an array location, in certain embodiments.

Any detectable label suitable for detection of an interaction or biological activity in a system can be appropriately selected and utilized by the artisan (e.g. certain detectable labels are described herein). In some embodiments, a known amount of label is linked to a target nucleic acid or counterpart nucleic acid (e.g., sometimes the label is stoichiometric). An amount of detectable label linked to a counterpart nucleic acid can be determined at a location on an array, for example, and an amount of the counterpart nucleic acid can be determined based on the amount of label detected.

In some embodiments target nucleic acid species can be further analyzed by nucleotide sequencing. Any suitable sequencing method can be utilized. In some embodiments, nucleotide sequencing may be by single nucleotide sequencing methods and processes. Single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in International PCT Patent Application Number PCT/US2009/031169 filed Jan. 15, 2009, published as publication no. WO 2009/091934 on Jul. 23, 2009, and incorporated herein by reference, in its entirety.

Examples of sequencing platforms include, without limitation, the 454 platform (Roche) (Margulies, M. et al. 2005 Nature 437, 376-380), Illumina Genomic Analyzer (or Solexa platform) or SOLID System (Applied Biosystems) or the Helicos True Single Molecule DNA sequencing technology (Harris T D et al. 2008 Science, 320, 106-109), the single molecule, real-time (SMRTTM) technology of Pacific Biosciences, and nanopore sequencing (Soni G V and Meller A. 2007 Clin Chem 53: 1996-2001). Such platforms allow sequencing of many nucleic acid molecules isolated from a specimen at high orders of multiplexing in a parallel manner (Dear Brief Funct Genomic Proteomic 2003; 1: 397-416). Each of these platforms allow sequencing of clonally expanded or non-amplified single molecules of nucleic acid fragments.

In some embodiments, target nucleic acid species can be analyzed by a single nucleotide sequencing technology known as pyro-sequencing. Pyro-sequencing is a method of DNA sequencing by synthesis. Sequencing by synthesis involves taking a single strand of DNA and synthesizing the complimentary strand enzymatically in a reaction, which is coupled to a chemiluminescent enzyme. Successful incorporation of a base liberates a pyrophosphate (PPi), which is converted into ATP, which then produces visible light through a reaction with luciferin. A camera detects the production of the visible light. The amount of light liberated is proportional to the amount of ATP produced. A number of pyro-sequencing methods and devices are available to the artisan, including, by way of non-limiting example, the Genome Sequencer FLX with GS FLX Titanium series reagents by 454 Life Sciences, a Roche company (Branford, Conn.).

In some embodiments, single nucleotide sequencing may be by the use of a nanopore device. Advances in nucleic acid analysis technology have included the use of nanopore technology to determine, for example, the sequence of a nucleic acid. A nanopore is a hole on the order of 1 nanometer in internal diameter in either a piece of silicon or naturally occurring as a transmembrane protein. When a nanopore is immersed in a conducting fluid and a voltage is applied, an electric current due to conduction of ions through the nanopore is observed. The amount of current is sensitive to the size of the nanopore. As DNA molecules pass through a nanopore, the DNA causes a partial blockage that may change the magnitude of the current, which passes through the nanopore. Detection of which nucleotide is flowing through the pore at any given moment is also possible due to the differences in the dimensions of each nucleotide, as the DNA is passed through the nanopore. The change in the current through the nanopore as the DNA molecule passes through the nanopore represents a direct reading of the DNA sequence. One such method of single nucleotide sequencing using a nanopore device is described in International PCT Patent Application Number PCT/US2009/031169 filed Jan. 15, 2009, published with publication no. WO 2009/091934 on Jul. 23, 2009, and incorporated herein by reference, in its entirety.

The amount of a particular target nucleic acid is quantified in certain embodiments. In some embodiments the amount of target nucleic acid captured can be determined from the amount of a counterpart added to a sample. When a known amount of a particular counterpart species is mixed with target, the amount of target can be calculated from the amount of counterpart detected after dynamic range compression. For example, counterpart can be mixed with target, the mixture can be contacted with an array having an address populated with a capture nucleic acid that specifically hybridizes to the counterpart species and its target species, and the amount of counterpart species hybridized at the address can be determined (e.g., by a single molecule sequencing technique). In some embodiments, the amounts of target species and counterpart species are determined and a ratio of the two is calculated. The amount of the target species can be inferred, extrapolated or determined by the amount of counterpart species or the ratio (counterpart species to target species or target species to counterpart species) in certain embodiments.

Examples of Embodiments of the Technology

Provided hereafter are non-limiting examples of embodiments of the technology.

1A. A method for quantifying amounts of target nucleic acids of a biological sample, which comprises:
   a. preparing a mixture by contacting (i) a plurality of target nucleic acids of a biological sample (targets) with (ii) a known amount of a counterpart nucleic acid for each of the targets (counterparts),
   wherein each counterpart comprises (i) a nucleotide sequence substantially identical to its target, and (ii) a feature that distinguishes each counterpart from its target, under conditions in which the targets hybridize to their counterparts;
   b. compressing the dynamic range of the targets in the mixture;
   c. determining the amount of each target and counterpart; and
   d. quantifying the amount of each target by the amount in (c).

1B. A method for identifying target nucleic acids of a biological sample, which comprises:
   a. preparing a mixture by contacting (i) a plurality of target nucleic acids of a biological sample (targets) with (ii) a known amount of a counterpart nucleic acid for each of the targets (counterparts),
   wherein each counterpart comprises (i) a nucleotide sequence substantially identical to its target, and (ii) a feature that distinguishes each counterpart from its target, under conditions in which the targets hybridize to their counterparts;
   b. compressing the dynamic range of the targets in the mixture; and
   c. identifying each target and counterpart.

1C. A method for compressing the dynamic range of target nucleic acids of a biological sample, which comprises:
   a. preparing a mixture by contacting (i) a plurality of target nucleic acids of a biological sample (targets) with (ii) a known amount of a counterpart nucleic acid for each of the targets (counterparts),
   wherein each counterpart comprises (i) a nucleotide sequence substantially identical to its target, and (ii) a feature that distinguishes each counterpart from its target, under conditions in which the targets hybridize to their counterparts;
   b. contacting the mixture with a set of capture nucleic acids, wherein (i) each capture nucleic acid in the set specifically hybridizes to a target and counterpart, (ii) each capture nucleic acid in the set hybridizes with substantially the same strength to the target and counterpart to which it specifically hybridizes; and (iii) the amount of each capture nucleic acid is less than highest amount of a target of the biological sample; whereby the dynamic range of the targets is compressed.

2. The method of any one of embodiments 1A, 1B and 1C, wherein the targets and counterparts are amplified before (b).
3. The method of any one of embodiments 1A, 1B and 1C, wherein the targets and counterparts are amplified after (b).
4. The method of any one of the preceding embodiments, wherein the feature in the counterpart is a one-nucleotide substitution in the sequence substantially identical to its target.
5. The method of any one of the preceding embodiments, wherein the feature in the counterpart is one or more additional nucleotides appended to the nucleotide sequence substantially identical to its target.
6. The method of any one of the preceding embodiments, wherein the ratio of the amount of each target to the amount of its counterpart is between about 1:10 and about 10:1.
7. The method of embodiment 1A or embodiment 1B, wherein (b) comprises contacting the mixture with a set of capture agents, wherein:
each agent specifically captures each target and its counterpart, and
the amount of each of the capture agents is within a range that compresses the dynamic range of the targets in the mixture.
8. The method of embodiment 7, wherein the array of capture agents is on a solid support.
9. The method of embodiment 7 or 8, wherein the capture agent interacts with the target and the counterpart with substantially equal affinity.
10. The method of any one of embodiments 7, 8 or 9, wherein each capture agent is a capture nucleic acid that comprises a polynucleotide sequence complementary to a nucleotide sequence of a target.
11. The method of embodiment 10, wherein the target-capture agent melting temperature (Tm) differs from the counterpart-capture agent Tm by less than or equal to one degree Celsius.
12. The method of any one of embodiments 7-10, wherein the amounts of any two capture agents of the array differ by less than or equal to 50%.
13. The method of embodiment 1B or 1C, wherein the sequence of the target is subsequently determined.
14. The method of embodiment 13, wherein the sequence of the target is determined by analyzing the target with a nanopore device.
15. The method of embodiment 1A or 1B, wherein the counterparts are separated from the targets after (b).
16. The method of embodiment 15, wherein the counterparts or targets comprise a capture moiety that binds to a capture agent.
17. The method of embodiment 1C, which comprises separating the counterparts from the targets after (b).
18. The method of embodiment 17, wherein the counterparts or targets comprise a capture moiety that binds to a capture agent.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present technology has been specifically disclosed by representative embodiments and optional features, modification and variation of the concepts herein disclosed may be resorted to by those skilled in the art, and such modifications and variations are considered within the scope of this technology.

Embodiments of the technology are set forth in the claims that follow.

What is claimed is:

1. A method for detecting a low abundance target nucleic acid in a biological sample comprising a plurality of target nucleic acid species comprising high abundance target nucleic acid species and low abundance target nucleic acid species, wherein the low abundance target nucleic acid is from low abundance target nucleic acid species and comprises a nucleotide sequence of interest, the method comprising:
   a) preparing a mixture by contacting the biological sample with a plurality of counterpart nucleic acids, wherein:
      the amount of each of the counterpart nucleic acids in the mixture is known and each of the counterpart nucleic acids comprises a nucleotide sequence at least 95% identical to its corresponding target nucleic acid species of the plurality of target nucleic acid species, and a feature that distinguishes each of the counterpart nucleic acids from its corresponding target nucleic acid species of the plurality of target nucleic acid species;
   b) contacting the mixture with a set of capture nucleic acids, wherein:
   (i) each capture nucleic acid in the set specifically hybridizes to one target nucleic acid species of the plurality of target nucleic acid species and its corresponding counterpart nucleic acid of the plurality of counterpart nucleic acids, thereby forming hybridized target nucleic acid species and hybridized counterpart nucleic acids,
      wherein the hybridized target nuclei acid species include the high abundance target nucleic acid species hybridized to their corresponding capture nucleic acids of the set of capture nucleic acids and the low abundance target nucleic acid species hybridized to their corresponding capture nucleic acids of the set of capture nucleic acids,
- (ii) relative to the amount of the low abundance target nucleic acid in the mixture, the capture nucleic acid of the set of capture nucleic acids for the low abundance target nucleic acid in the mixture is present in a saturating amount; and
- (iii) relative to the amounts of the high abundance target nucleic acid species in the mixture, the capture nucleic acids of the set of capture nucleic acids for the high abundance target nucleic acid species in the mixture are present in non-saturating amounts;

c) separating the hybridized target nucleic acid species from the hybridized counterpart nucleic acids after step b), d) detecting the hybridized target nucleic acid species and the hybridized counterpart nucleic acids, whereby the low abundance target nucleic acid in the biological sample is detected.

2. The method of claim 1, wherein each of the target nucleic acid species and each of the counterpart nucleic acids are amplified before step (b).

3. The method of claim 1, wherein the feature that distinguishes each of the counterpart nucleic acids from its corresponding target nucleic acid species of the plurality of target nucleic acid species is that, relative to the sequence of the its corresponding target nucleic acid species of the plurality of target nucleic acid species, there is a one-nucleotide substitution in the sequence of each of the counterpart nucleic acids.

4. The method of claim 1, wherein the ratio of the amount of each of the target nucleic acid species to the amount of its corresponding counterpart nucleic acid of the counterpart nucleic acids in the mixture is between about 1:10 and about 10:1.

5. The method of claim 1, wherein the capture nucleic acids are in an array on a solid support.

6. The method of claim 1, wherein a difference of the melting temperature (Tm) of each of the target nucleic acid species hybridized to its corresponding capture nucleic acid of the set of capture nucleic acids in step (b) between the Tm of its corresponding counterpart nucleic acid hybridized to the its corresponding capture nucleic acid of the set of capture nucleic acids in step (b) is less than or equal to one degree Celsius.

7. The method of claim 1, wherein the sequences of the target nucleic acid species are subsequently determined.

8. The method of claim 7, wherein the sequences of the target nucleic acid species are determined by analyzing the target nucleic acid species with a nanopore device.

9. The method of claim 1, wherein the amounts of the capture nucleic acids differ from each other by 10% or less than 10%.

10. The method of claim 9, wherein the less than 10% is 5% or less than 5%.

11. The method of claim 1, wherein each capture nucleic acid in the set of capture nucleic acid hybridizes to its corresponding target nucleic acid species of the plurality of target nucleic acid species and its corresponding counterpart nucleic acid of the counterpart nucleic acids with an equal affinity.

12. The method of claim 1, wherein the method further comprises
- e) measuring the amounts of the low abundance target nucleic acid species hybridized to their corresponding capture nucleic acids of the set of capture nucleic acids and the hybridized counterpart nucleic acids, wherein each capture nucleic acid in the set of capture nucleic acid hybridizes to its corresponding target nucleic acid species of the plurality of target nucleic acid species and its corresponding counterpart nucleic acid of the counterpart nucleic acids with an equal affinity;
- f) quantifying the amount of each of the low abundance target nucleic acid species in the biological sample based on the relative amounts of each of the low abundance target nucleic acid species hybridized to its corresponding capture nucleic acid of the set of capture nucleic acids and its corresponding counterpart nucleic acid from the hybridized counterpart nucleic acids.

13. The method of claim 12, wherein the capture nucleic acids are in an array on a solid support.

14. The method of claim 12, wherein a difference of the melting temperature (Tm) of each of the target nucleic acid species hybridized to its corresponding capture nucleic acid of the set of capture nucleic acids in step (b) between the Tm of its corresponding counterpart nucleic acid hybridized to the its corresponding capture nucleic acid of the set of capture nucleic acids in step (b) is less than or equal to one degree Celsius.

15. The method of claim 12, wherein the amounts of the capture nucleic acids differ from each other by 10% or less than 10%.

16. The method of claim 15, wherein the less than 10% is 5% or less than 5%.

* * * * *